US006846702B1

(12) United States Patent
Barth

(10) Patent No.: US 6,846,702 B1
(45) Date of Patent: Jan. 25, 2005

(54) NANOPORE CHIP WITH N-TYPE SEMICONDUCTOR

(75) Inventor: Phillip W. Barth, Portola Valley, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 10/693,060

(22) Filed: Oct. 24, 2003

(51) Int. Cl.[7] .............................................. H01L 21/44
(52) U.S. Cl. ...................... 438/108; 438/21; 435/287.2
(58) Field of Search .................... 438/17, 21, 108–127; 435/285.2, 287.2, 288.5

(56) References Cited

U.S. PATENT DOCUMENTS 6,413,792 B1    7/2002  Sauer et al.
6,428,959 B1 *  8/2002  Deamer ........................ 435/6
2003/0013186 A1 * 1/2003  Martin et al. ............ 435/287.2

FOREIGN PATENT DOCUMENTS

WO      WO01/81896      1/2001
WO      WO01/81908      1/2001

* cited by examiner

*Primary Examiner*—Matthew Smith
*Assistant Examiner*—Calvin Lee
(74) *Attorney, Agent, or Firm*—Timothy H. Joyce

(57) ABSTRACT

An apparatus and method for making a nanopore chip exhibiting one of low photosensitivity, low electrical noise, and low electrical drift. The apparatus provides a thin insulating diaphragm containing a nanopore, the diaphragm being supported on a rigid semiconductor frame, the semiconductor frame having N-type doping in those regions which are to be capacitively coupled to an ionic solution. Also disclosed is a method of making the apparatus.

11 Claims, 2 Drawing Sheets

NANOPORE CHIP WITH N-TYPE SEMICONDUCTOR

TECHNICAL FIELD

The invention relates generally to the field of nanopores and more particularly to an apparatus and method for making a nanopore chip exhibiting one of low photosensitivity, low electrical noise, and low electrical drift.

BACKGROUND

Manipulating matter at the nanometer scale is important for many electronic, chemical and biological advances (See Li et al., "Ion beam sculpting at nanometer length scales", Nature, 412: 166–169, 2001). Such techniques as "ion beam sculpting" have shown promise in fabricating molecule scale holes and nanopores in thin insulating membranes. These pores have also been effective in localizing molecular-scale electrical junctions and switches (See Li et al., "Ion beam sculpting at nanometer length scales", Nature, 412: 166–169, 2001).

Artificial nanopores have been fabricated by a variety of research groups with a number of materials. Generally, the approach is to fabricate these nanopores in a solid-state material or a thin freestanding diaphragm of material supported on a frame of thick silicon to form a nanopore chip. Some materials that have been used to date for the diaphragm material include silicon nitride and silicon dioxide. These materials are insulators, with resistivity typically greater than $10^{10}$ Ohm-cm. In contrast, silicon is a semiconductor with a resistivity less than $10^4$ Ohm-cm, and for practical purposes can be considered to be a near short circuit in relation to the insulating diaphragm material.

Data is typically obtained from an artificial nanopore by placing the nanopore in an aqueous ionic solution of potassium chloride (KCl), commonly referred to as a "buffer" solution, the solution containing molecules of a polynucleotide such as double-stranded DNA. See, for example, "DNA molecules and configurations in a solidstate nanopore microscope," by Jiali Li, Marc Gershow, Derek Stein, Eric Brandin, and J. A. Golovchenko, Nature Materials, Vol. 2, September 2003, pp 611–615, which is incorporated herein in its entirety by reference. FIG. 1b from that reference is reproduced herein as FIG. 1. With reference to FIG. 1, during use a voltage V is applied across the nanopore by electrodes located in the "Cis" and "Trans" volumes, and the resulting current is measured as an "Ionic current signal."

Communication between the inventor and the authors of the above reference revealed that a problem with the use artificial nanopores fabricated to date has been high photosensitivity, necessitating taking data in the dark. Therefore an approach is needed which provides low photosensitivity. It is also desirable to minimize noise and drift in the ionic current signal.

Other investigators have proposed building nanopores in semiconducting membranes with surface insulators on the semiconductors. See, for example, U.S. Pat. No. 6,413,792, "Ultra-fast Nucleic Acid Sequencing Device and a Method for Making and Using Same," and associated world filings WO01/81908 and WO01/81896. However, because the semiconductor in such a membrane provides a near short circuit in comparison to an insulator, the characteristics of the resulting ionic current signal are severely degraded if such a semiconducting membrane is used in the apparatus shown in FIG. 1

These and other problems with the prior art processes and designs are obviated by the present invention. The references cited in this application infra and supra, are hereby incorporated in this application by reference. However, cited references or art are not admitted to be prior art to this application.

SUMMARY OF THE INVENTION

The invention provides an apparatus and method for nanopore construction.

The apparatus comprises a nanopore chip comprising a nanopore disposed in an insulating diaphragm, the diaphragm being supported by a rigid frame, the rigid frame comprising an N-type semiconductor in those portions of the nanopore chip which are intended to be capacitively coupled to an ionic solution.

The invention also provides a method of making the apparatus. The method of making the apparatus comprises fabricating a nanopore chip by providing a semiconductor substrate, providing N-type doping at those portions of the substrate which are to be capacitively coupled to an ionic solution, forming an insulating diaphragm supported by the substrate, forming a nanopore disposed in the diaphragm.

The steps of the above method may be varied in any logically consistent fashion. For example, the nanopore may be formed before or after the diaphragm is formed. The providing of N-type doping may occur before or after the diaphragm is formed.

DETAILED DESCRIPTION OF THE INVENTION

Before describing the present invention in detail, it is to be understood that this invention is not limited to specific compositions, method steps, or equipment, as such may vary. It is also to be understood that the terminology used herein is for the purpose of describing particular embodiments only, and is not intended to be limiting. Methods recited herein may be carried out in any order of the recited events that is logically possible, as well as the recited order of events.

Unless defined otherwise below, all technical and scientific terms used herein have the same meaning as commonly understood by one of ordinary skill in the art to which this invention belongs. Still, certain elements are defined herein for the sake of clarity. In the event that terms in this application are in conflict with the usage of ordinary skill in the art, the usage herein shall be controlling.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits; ranges excluding either or both of those included limits are also included in the invention.

Methods recited herein may be carried out in any order of the recited events that is logically possible, as well as the recited order of events.

It must be noted that, as used in this specification and the appended claims, the singular forms "a", "an," "the," and "one of" include plural referents unless the context clearly dictates otherwise.

The term "about" refers to being closely or approximate to, but not exactly. A small margin of error is present. This margin of error would not exceed plus or minus the same integer value. For instance, about 0.1 micrometers would mean no lower than 0 but no higher than 0.2.

The term "nanopore" refers to any pore or hole between at least a pair of electrodes or a hole in a solid substrate. Nanopores can range in size and can range from about 1 nm to about 300 nm. Most effective nanopores have been roughly around 2 nm.

The term "adjacent" refers to anything that is near, next to or adjoining. For instance, a tensile layer may be near a compressive layer, next to a compressive layer or adjoining a compressive layer.

Figure 1:
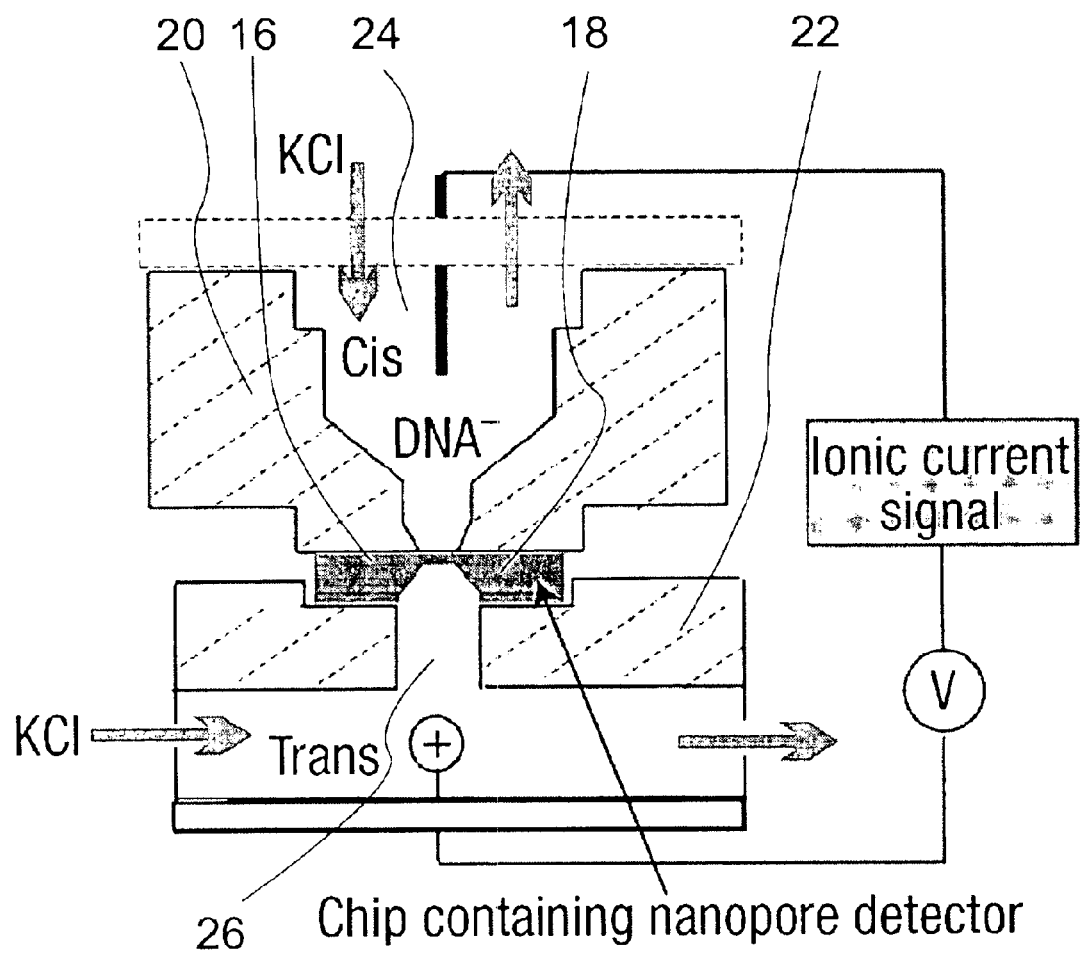
FIG. 1 reproduces FIG. 1b from "DNA molecules and configurations in a solidstate nanopore microscope," by Jiali Li, Marc Gershow, Derek Stein, Eric Brandin, and J. A. Golovchenko, Nature Materials, Vol. 2, September 2003, pp 611–615

FIG. 1 shows a cross section the apparatus of the present invention packaged for use with associated ionic solutions and electronics. The figure is not to scale, and some features are greatly exaggerated for purposes of description. The nanopore is very small in comparison to the width of the diaphragm and is not explicitly shown in the drawing, but that nanopore sits in the thin diaphragm atop the "Chip containing nanopore detector," herein called a "nanopore. chip."

Figure 2:
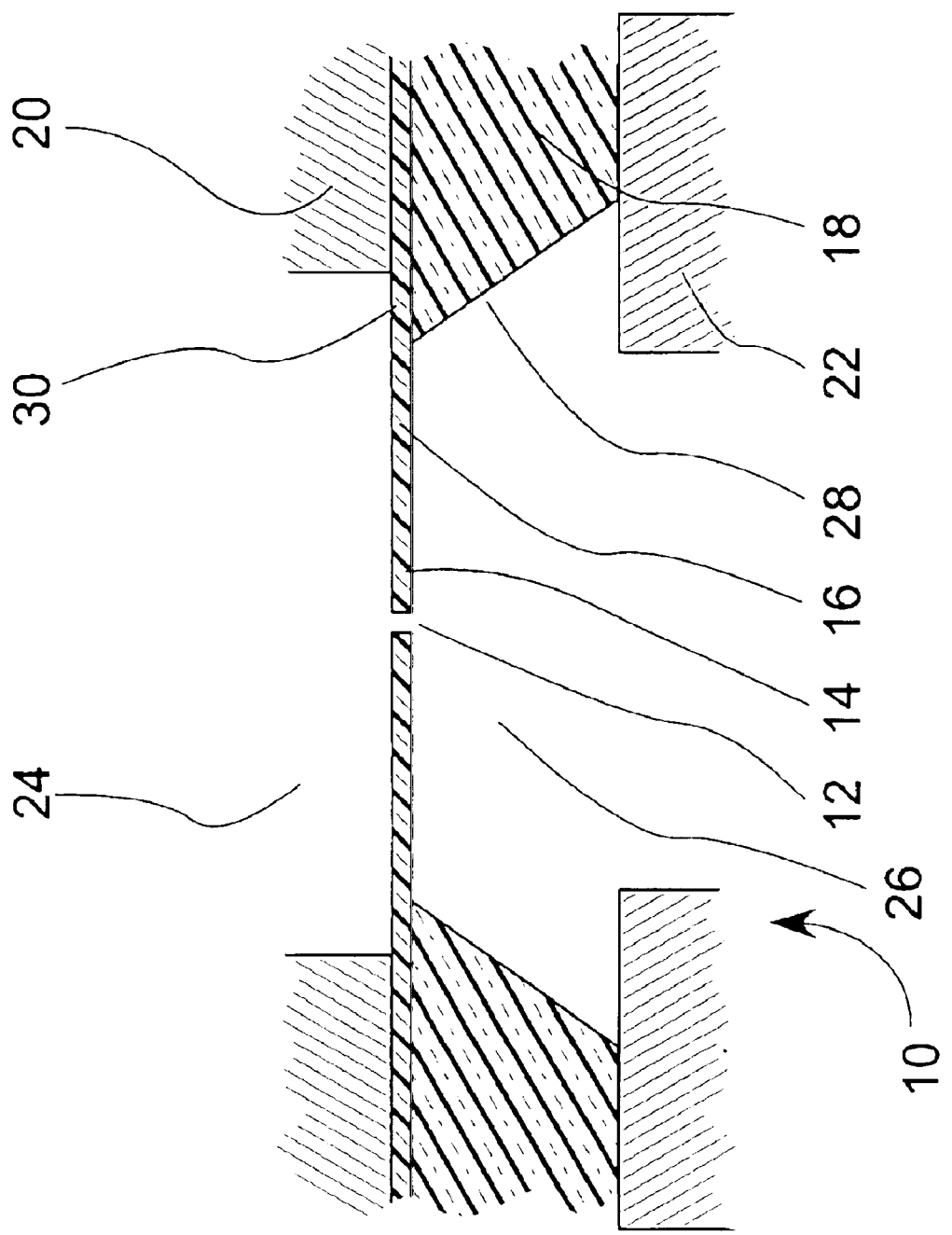
FIG. 2 is a cross section of a nanopore chip comprising the apparatus of the present invention.

FIG. 2 shows a corss section of theapparatus of the present invention with some associated packaging elements.

A detailed description of the operation of the apparatus of the invention is as follows, with reference to FIGS. 1 and 2. A voltage V, typically on the order of 120 millivolts, is applied between the "Cis"volume 24 and "Trans" volume 26 of aqueous ionic KCl solution. DNA molecules, which have a negative charge and are labeled "DNA−" to denote that charge, sit in the CIS volume 24 and are drawn by the voltage difference between the Cis and Trans volumes 24 and 26 to the nanopore 12 in the thin insulating diaphragm 14 atop the nanopore chip 10, through that nanopore 12, and into the Trans volume 26. At the same time an ionic stream, not shown, comprising negatively charged hydrated chlorine ions flow from Cis to Trans, and an ionic stream, not shown, comprising positively charged hydrated potassium ions flows from Trans to Cis. Packaging element 20 confines the ionic solution to the Cis volume 24 while packaging element 22 confines the ionic solution to the Trans volume 26.

The total measured "ionic current signal" comprises not only charge flows due to the DNA, the chlorine ions, and the potassium ions, but also comprises undesired displacement currents having transient characteristics (called "AC characteristics") with some magnitude and some frequency spectrum, but having zero net long-term characteristics (called "DC characteristics"). These displacement currents occur across the insulating diaphragm 14 in which the nanopore 12 sits, across the capacitively-coupled interfaces 28 between the semiconductor frame 18 and the Trans volume 26, and across the capacitively coupled interface 30 between the semiconductor frame 18 and the Cis volume 24

At the same time, the current through the nanopore 12 has both a DC characteristic and an AC characteristic, the AC characteristic having some frequency spectrum.

If the desired ionic current through the nanopore overlaps in frequency with the undesired displacement current, the desired signal is degraded to some extent.

To minimize the displacement current, one approach is to minimize capacitance either through packaging design, through modification to the nanopore chip for example as in patent application Ser. No. 10/693,064, APPARATUS AND METHOD FOR MAKING A LOW CAPACITANCE ARTIFICIAL NANOPORE, which is incorporated herein in its entirety by reference), or both.

However, some capacitive coupling of ionic solution to the semiconductor frame 18 of nanopore chip 10 still occurs, especially in the region 28 beneath the diaphragm where bare etched silicon adjacent the diaphragm edge touches the Trans volume 26, and also in regions of the Cis volume 24 where liquid contact occurs to thin insulator regions on surfaces of the semiconductor chip.

Previous nanopore chips have been fabricated using p-type silicon by the authors of the above-referenced "DNA molecules and configurations in a solidstate nanopore microscope," by Jiali Li, Marc Gershow, Derek Stein, Eric Brandin, and J. A. Golovchenko, Nature Materials, Vol. 2, September 2003, pp 611–615. It has been found that these chips exhibit high photosensitivity of the measured ionic current signal, thus requiring dark ambient conditions during measurement in order to obtain useful data.

It is the present inventor's belief that such photosensitivity is the result of capacitive displacement currents resulting from hole-electron pair generation in a depletion region near the bare surface of the p-type silicon, corresponding to region 28 of the present invention, and near insulator surfaces corresponding to region 30 of the present invention. In addition it is the inventor's belief that thermal variations and electrically induced variations in depletion region width cause transient currents and signal drift with time constants on the order of hours, thus degrading the measured signals.

The inventor has proposed the use of n-type silicon instead of p-type silicon to fabricate the semiconductor frame 18 of nanopore chips in the belief that such chips would have an accumulation region, rather than a depletion region, near region 28 and region 30, and that such chips would exhibit greatly reduced photosensitivity of the ionic current. Such chips have been fabricated, and the expected reduction in photosensitivity has been achieved. As of this writing, no measurements of transients and long-term drift have been conducted. The present invention is expected to show utility in reducing transients, electrical noise, and electrical drift.

Experimental verification of the utility of the present invention was gained using a silicon frame 18 comprising n-type silicon doped with phosphorous and having a resistivity in the range of 1–50 Ohm-cm. Other n-type dopants known in the art, including but limited to arsenic, may be used, and other resistivities may be used, including but not limited to resistivities from 0.002 Ohm-cm to 10,000 Ohm-cm. Other n-type semiconductors may be used, including but not limited to germanium and gallium arsenide, and for such other n-type semiconductors known n-type dopants may be used, including but not limited to phosphorous and arsenic.

It will be appreciated that, while the present invention is aimed toward utility in fabrication of nanopore structures, it may prove to have utility for fabrication of other devices both known and unknown in which an insulating diaphragm supported on a semiconductor frame is placed between two volumes of ionic conductor. Such devices include devices with microscale and nanoscale dimensions. Microscale dimensions are defined to include dimensions from 100 nm to 1 mm, and nanoscale dimensions are defined to include dimension from 0.1 nm to 1 um.

Thus, the present invention comprises a chip apparatus for use in a package comprising an ionic solution, the chip apparatus having an insulating diaphragm, one of a microscale and a nanoscale device disposed one of in or on the insulating diaphragm, and a semiconductor frame supporting the insulating diaphragm, wherein those portions of the semiconductor frame which are to be capacitively coupled to an ionic solution, the ionic solution also to be electrically coupled to the one of a microscale and a nanoscale device, comprise an n-type semiconductor, comprising typically n-type silicon.

Variations on the above apparatus will occur to those skilled in the art without departing from the scope and spirit of the present invention.

While FIG. 1 shows the cavity on the bottom side of the diaphragm extending entirely through the thickness of the semiconductor frame, this is not a necessity of the invention, and instead the cavity beneath the diaphragm may occupy a limited portion of the thickness of the semiconductor frame.

A limited area of p-type semiconductor may intrude into the portions of the semiconductor frame 18 which are to be capacitively coupled to an ionic solution without significantly degrading the performance of the present invention. Such regions are expected to increase photosensitivity, noise, and drift, but such increases will be tolerated as part of desirable performance tradeoffs when, for example, active electronic elements are integrated into the nanopore chip.

A limited area of semiconductor may intrude into the insulating diaphragm 14 without significantly degrading the performance of the present invention. Such regions are expected to increase photosensitivity, noise, and drift, but such increases will be tolerated as part of desirable performance tradeoffs when, for example, active electronic elements are integrated into the nanopore chip.

A limited area of metal may intrude into the insulating diaphragm 14 without significantly degrading the performance of the present invention. Such regions are expected to increase photosensitivity, noise, and drift, but such increases will be tolerated as part of desirable performance tradeoffs when, for example, active electronic elements are integrated into the nanopore chip.

The present invention also comprises a method of fabricating a chip apparatus for use in a package comprising an ionic solution, comprising providing a semiconductor frame, providing n-type semiconductor regions comprising those portions of the semiconductor frame which are to be capacitively coupled to an ionic solution, providing an insulating diaphragm supported by the semiconductor frame, and providing one of a microscale and a nanoscale device disposed one of in or on the insulating diaphragm, the ionic solution also to be electrically coupled to the one of a microscale and a nanoscale device.

It will be appreciated that the fabrication sequence described above is by way of example only, and that there are others techniques well known to those skilled in the art which may be used to arrive at the same final apparatus.

It will be appreciated that the fabrication of a nanopore may be accomplished by means other than focused ion beam drilling and argon ion beam sculpting described in Li et al., "Ion beam sculpting at nanometer length scales", *Nature*, 412: 166–169, 2001. For example, other known means of fabricating a nanopore include masking with a nanoparticle followed by layer evaporation around the masking nanoparticle, next followed by removal of the nanoparticle and etching within the hole which had been masked by the nanoparticle. Such techniques, both known and unknown, may be used to fabricate nanopores as part of the apparatus and method of the present invention.

I claim:

1. A method of fabricating a chip for use in a package comprising an ionic solution, the method comprising providing a semiconductor frame, providing n-type semiconductor regions comprising those portions of the semiconductor frame which are to be capacitively coupled to an ionic solution, providing an insulating diaphragm supported by the semiconductor frame, and providing one of a microscale and a nanoscale device disposed one of in or on the insulating diaphragm, the ionic solution also to be electrically coupled to the one of a microscale and a nanoscale device.

2. A method as claimed in claim 1 wherein the n-type semiconductor comprises silicon.

3. A method as claimed in claim 2 wherein the silicon is doped with a dopant chosen from a group comprising phosphorous and arsenic.

4. A method as claimed in claim 1 wherein the n-type semiconductor is chosen from a group comprising germanium and gallium arsenide.

5. A method as claimed in claim 1 wherein the n-type semiconductor is doped with a dopant chosen from a group comprising phosphorous and arsenic.

6. A chip apparatus for use in a package comprising an ionic solution, the chip comprising an insulating diaphragm, one of a microscale and a nanoscale device disposed one of in or on the insulating diaphragm, and a semiconductor frame supporting the insulating diaphragm, wherein those portions of the semiconductor frame which are to be capacitively coupled to an ionic solution, the ionic solution also to be electrically coupled to the one of a microscale and a nanoscale device, comprise an n-type semiconductor.

7. A chip apparatus as claimed in claim 6 wherein the n-type semiconductor comprises silicon.

8. A chip apparatus as claimed in claim 7 wherein the silicon is doped with a dopant chosen from a group comprising phosphorous and arsenic.

9. A chip apparatus as claimed in claim 6 wherein the n-type semiconductor is chosen from a group comprising germanium and gallium arsenide.

10. A chip apparatus as claimed in claim 9 wherein the n-type semiconductor is doped with a dopant chosen from a group comprising phosphorous and arsenic.

11. A chip apparatus as claimed in claim 6 wherein the one of a microscale and a nanoscale device comprises a nanopore.

* * * * *